(12) United States Patent
Radulescu et al.

(10) Patent No.: US 9,743,881 B2
(45) Date of Patent: Aug. 29, 2017

(54) PHOTOACOUSTIC CATHETER FOR FUNCTIONAL-IMAGING-BASED ABLATION MONITORING

(75) Inventors: Emil Radulescu, Ossining, NY (US); Sheng-Wen Huang, Ossining, NY (US); Ramon Erkamp, Yorktown Heights, NY (US); Ladislav Jankovic, Fishkill, NY (US); Yan Shi, White Plains, NY (US); Khalid Shahzad, Shrub Oak, NY (US)

(73) Assignee: Koninklijke Philips N.V., Eindhoven (NL)

( * ) Notice: Subject to any disclaimer, the term of this patent is extended or adjusted under 35 U.S.C. 154(b) by 1004 days.

(21) Appl. No.: 14/007,029

(22) PCT Filed: Mar. 27, 2012

(86) PCT No.: PCT/IB2012/051452
§ 371 (c)(1),
(2), (4) Date: Dec. 4, 2013

(87) PCT Pub. No.: WO2012/131577
PCT Pub. Date: Oct. 4, 2012

(65) Prior Publication Data
US 2014/0088418 A1 Mar. 27, 2014

Related U.S. Application Data

(60) Provisional application No. 61/468,718, filed on Mar. 29, 2011.

(51) Int. Cl.
*A61B 5/00* (2006.01)
*A61B 18/14* (2006.01)
(Continued)

(52) U.S. Cl.
CPC .......... *A61B 5/4836* (2013.01); *A61B 5/0044* (2013.01); *A61B 5/0059* (2013.01);
(Continued)

(58) Field of Classification Search
CPC ... A61B 5/0093; A61B 5/0095; A61B 5/0097; A61K 49/0002
See application file for complete search history.

(56) References Cited

U.S. PATENT DOCUMENTS 6,515,346 B1    2/2003  Kemeny
2005/0156282 A1  7/2005  Palti
(Continued)

FOREIGN PATENT DOCUMENTS

EP    0282234 A1   9/1988
EP    1935332 A2   6/2008
(Continued)

OTHER PUBLICATIONS

Zhang, Hao F. et al "Functional Photoacoustic Microscopy for high-resolution and Noninvasive invivo Imaging", Nature Biotechnology, vol. 24, No. 7, Jul. 2006, pp. 848-851.
(Continued)

*Primary Examiner* — Serkan Akar

(57) ABSTRACT

Functional imaging for localization in biological tissue entails measuring a response in the tissue (240) to electromagnetic radiation. A catheter (200) for real-time monitoring of cardiac ablation is employed to distinguish a hemorrhage zone (232) from the sandwiching necrotic and healthy tissue, or to distinguish exogenous photoacoustic contrast agent from bordering native tissue. A pair of wavelengths is selected for differential absorption (244) of the radiation in, correspondingly, the hemorrhage zone or where the contrast agent exists, and relatively similar absorption elsewhere. Near infrared laser or LED light may be used photoacous-
(Continued)

tically to serially acquire (S310, S320) the two datasets to be compared, each representative of a time waveform. Alternatively, acquisition is for a pair of wavelength bands of microwave-induced thermoacoustic data. In either case, the members of the dataset pair are combined (110, 122) by subtraction or division to effect the piece-wise cancellation/enhancement for display (218) of the resulting signal in real time.

22 Claims, 4 Drawing Sheets

(51) Int. Cl.
A61B 18/18 (2006.01)
A61K 49/00 (2006.01)
A61B 18/00 (2006.01)
A61B 90/00 (2016.01)

(52) U.S. Cl.
CPC .......... *A61B 5/0084* (2013.01); *A61B 5/0095* (2013.01); *A61B 5/6852* (2013.01); *A61B 5/742* (2013.01); *A61B 18/1492* (2013.01); *A61B 18/18* (2013.01); *A61K 49/0002* (2013.01); *A61B 2018/00577* (2013.01); *A61B 2090/378* (2016.02); *A61B 2576/00* (2013.01)

(56) References Cited

U.S. PATENT DOCUMENTS

| 2008/0154257 A1 | 6/2008 | Sharareh et al. |
| 2010/0006536 A1 | 1/2010 | Kalvesten |
| 2010/0268042 A1* | 10/2010 | Wang .................. A61B 5/0059 600/322 |
| 2010/0280504 A1 | 11/2010 | Manzke |
| 2016/0317844 A1 | 11/2016 | Lupotti |

FOREIGN PATENT DOCUMENTS

| WO | 04000148 A2 | 12/2003 |
| WO | 2009090588 A1 | 7/2009 |
| WO | 2009150593 A1 | 12/2009 |
| WO | 2010020939 A2 | 2/2010 |
| WO | 2010146532 A1 | 12/2010 |

OTHER PUBLICATIONS

Talbert, Robert J. et al "Photoacoustic Discrimination of Viable and Thermally Coagulated Blood using a Two-Wavelength Method for Burn Injury Monitoring; Photoacoustic Blood Discrimination", Physics in Medicine and Biology, vol. 52, No. 7, Apr. 2007, pp. 1815-1829.

Yamazaki, Mutsuo et al "Measurement of Burn Depths in Rats using Multiwavelength Photoacoustic Depth Profiling", Journal of Biomedical Optics, vol. 10, No. 6, 2005.

Aizawa, Kazuya et al "Photoacoustic Monitoring of Burn Healing Process in Rats", Journal of Biomedical Optics, vol. 13, No. 6, 2008.

Zhang, H.F., et al., "imaging acute thermal burns by photoacoustic microscopy", Journal of Biomedical Optics 11(5), 054033 (Sep./Oct. 2006).

Aizawa, K., et al., "In vivo photoacoustic spectroscopic imaging of hemoglobin derivatives in thermally damaged tissue", Japanese Journal of Applied Physics 48 (2009).

Ventricular arrhythmias manual, used in hospital japan society of Cardiology Jul. 2010.

* cited by examiner

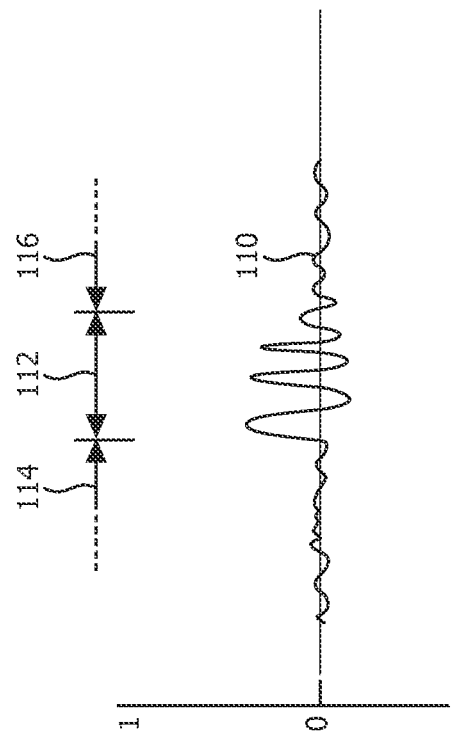
FIG. 1A
FIG. 1B
FIG. 1C
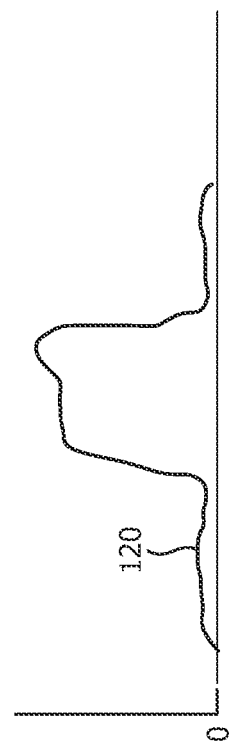
FIG. 1D

PHOTOACOUSTIC CATHETER FOR FUNCTIONAL-IMAGING-BASED ABLATION MONITORING

CROSS-REFERENCE TO PRIOR APPLICATIONS

This application is the U.S. National Phase application under 35 U.S.C. §371 of International Application No. PCT/IB2012/051452, filed on Mar. 27, 2012, which claims the benefit of U.S. Provisional Patent Application No. 61/468718, filed on Mar. 29, 2011. These applications are hereby incorporated by reference herein.

FIELD OF THE INVENTION

The present invention is directed to imaging for localization in biological tissue and, more particularly, to analyzing a response in the tissue to electromagnetic radiation.

BACKGROUND OF THE INVENTION

In the minimally-invasive treatment of cardiac arrhythmias, the radiofrequency (RF) ablation catheter is the most commonly-used therapy tool, and is referred to as the gold standard in trials of new ablation catheter designs. One major challenge of RF ablation is to actively control the ablation settings during treatment. Currently, the therapist relies on his or her own expertise to determine the optimal parameters for ablation, such as power, temperature, and duration. Note that these settings vary largely, due to sizable intra-patient differences of thickness of the local heart wall, perfusion, blood pressure and velocity, heart rhythm, etc. Although a highly-skilled therapist is able to achieve successes with this approach, it is not always the case, and there are serious consequences for the patient when an error is made.

The two major therapy-related problems result from either the under- or over-heating of the site. In the case of under-heating, the tissue is not sufficiently coagulated or the ablation lesion is not deep enough to form the arrhythmia-blocking lesion desired by the therapist. This can lead to persistent or recurring symptoms in the patient, and the requirement for subsequent treatment(s), longer periods of hospitalization, and greater risks of stroke and embolism. Redo ablation procedures are more difficult to perform, since the already treated areas are very hard to discriminate from insufficiently treated ones. The other extreme, over-heating, either causes rupturing of the tissue at the treatment site, releasing potentially life-threatening particles into the blood stream, or causes damage to neighboring organs and tissues. In the case where other organs are affected, fistulas can develop and these are often life-threatening (e.g., a fistula in the esophagus has roughly a 75% mortality rate).

There is prior art suggesting that photoacoustic measurements are generally useful for bum depth assessment. See Talbert, R. J et al. "Photoacoustic discrimination of viable and thermally coagulated blood using a two-wavelength method for burn injury monitoring," Physics in Medicine and Biology, vol. 52, no. 7, pp. 1815, 2007 (a multiple wavelength photoacoustic imaging method to discriminate coagulated and non-coagulated blood in a dermal bum phantom using statistical methods. The Talbert study finds a border between viable and necrotic skin tissue through photoacoustic imaging at two optical wavelengths. The necrotic tissue contains thermally coagulated blood which is visibly brown. The underlying inflamed tissue is characterized by the presence of viable, i.e., non-coagulated, blood which is red. Using planar blood layers, Talbert found the ratio of photoacoustic absorption at wavelengths of 543 nanometers (nm) and 633 nm, respectively, in non-coagulated blood to be 13.5:1; whereas, the ratio was 1.6:1 in coagulated blood. By statistical techniques, the border between the viable and necrotic condition of skin is located. There is also prior art suggesting that functional photoacoustic imaging is useful for hemoglobin oxygen saturation of single vessels. See Zhang, H. F. et al. "Functional photoacoustic microscopy for high-resolution and noninvasive in vivo imaging", Nature Biotechnology, Volume 24, Number 7, July 2006.

SUMMARY OF THE INVENTION

The present inventors have found that a hemorrhage ring (or zone) exists that separates necrotic cardiac tissue during ablation from the underlying healthy cardiac tissue. The cardiac RF ablation lesions are typically characterized by a visually pale white color indicating coagulation necrosis and are surrounded by a dark red zone indicating hemorrhage, i.e., the hemorrhage ring.

Irradiation at two appropriately selected wavelengths results in similar absorption both in the necrotic and the healthy tissue, but markedly different absorption in the hemorrhage zone.

Advantageously, the two wavelength-specific groups of acquired photoacoustic (PA) data can be combined so as to suppress or cancel the signal from the tissue surrounding the hemorrhage zone, leaving the hemorrhage zone signal relatively enhanced. The two groups of data can be acquired sequentially in a short sequence, e.g., about 15 microseconds ($\mu$s), for an atrium 10 mm in thickness, and the human atrium is typically several millimeters (mm) thick. Assuming 100 heart beats per minute, one cardiac cycle is about 600 milliseconds (ms). Cardiac motion is therefore minimal during the period and does not significantly affect combining of the data.

Display of the signal facilitates real-time monitoring of the RF cardiac ablation. Accordingly, functional imaging, which relates to physiology rather than anatomy or structure, is used in RF cardiac ablation monitoring.

In one aspect of the present invention, imaging is performed to monitor biological tissue ablation by distinguishing a hemorrhage zone, disposed between healthy tissue and ablated tissue, from the healthy and ablated tissue.

In a further aspect, the distinguishing involves combining data, acquired by electromagnetic irradiation at different frequencies or frequency bands, that serve as a measure of absorption of the electromagnetic radiation by the biological tissue.

As a yet further aspect, the combining enhances data magnitude in the hemorrhage zone relative to that for adjacent tissue.

In an additional aspect, an apparatus is configured for the irradiating, and/or the acquiring, and/or display of a signal representative of the combined data.

In another aspect, the apparatus can be implemented as one or more integrated circuits for being communicatively connected to a transducer for the acquiring, and/or an emitter for the irradiating, and/or a processor for generating the signal.

In a related aspect, the data to be combined is acquired successively, correspondingly one frequency or band at a time, before being combined.

As an alternative aspect, the combining serves to combine the data of a pair of frequencies or of a pair of frequency bands.

In a sub-aspect, the combining is performed by subtraction and/or division.

In another sub-aspect, each of the two constituents being combined to form a pair is representable as a time waveform.

In one other sub-aspect, an apparatus includes a processor configured for subtracting to yield a difference signal and/or dividing to yield a quotient signal, and a display. The apparatus is further configured for showing, on the display, the difference and/or quotient signal.

As yet another sub-aspect, the combining is performed by subtraction.

In a related aspect, the monitoring is performed in real time.

In a sub-aspect, the real-time monitoring is of cardiac ablation.

In a different aspect, a depth-independent equalization is performed that takes account of wavelength-dependent attenuation in the hemorrhage zone.

In one other aspect, the imaging is performed by means of a catheter.

In a further related aspect, administered photoacoustic contrast agent is located by irradiating, in series, using either different frequencies, or different frequency bands, of electromagnetic radiation for which difference in, or ratio of, the response distinguishes over that for bordering, native tissue.

In yet another related aspect, a catheter includes a transducer, and an electromagnetic energy emitter concentrically aligned with an acoustic-response-flow portion acquired by the transducer for photoacoustic processing.

In a yet further related aspect, a catheter includes an elongated housing having an ablation end; and, at said end, a transparent window to which a layer is added. The layer is designed so as to serve as a radiofrequency electrode and yet allow for the passage of ultrasound and light through the window for photoacoustic imaging.

What is proposed herein is realizable as methods, devices for performing the methods, computer programs for carrying out the functionality of the devices, signals for conveying the functionality, and/or methods for generating the signals. A method for generating a signal comprises varying an electrical current applied to at least one of: a) a wire input to said device; and b) an antenna for transmitting, so as to, by the varying, generate the signal.

Details of the novel, ablation-monitoring, functional imaging technology are set forth further below, with the aid of the following drawings.

DESCRIPTION OF THE DRAWINGS

FIGS. 1A-1D are graphs of exemplary time waveforms representing photoacoustic absorption magnitude data;

DETAILED DESCRIPTION OF EMBODIMENTS

Figure 2:
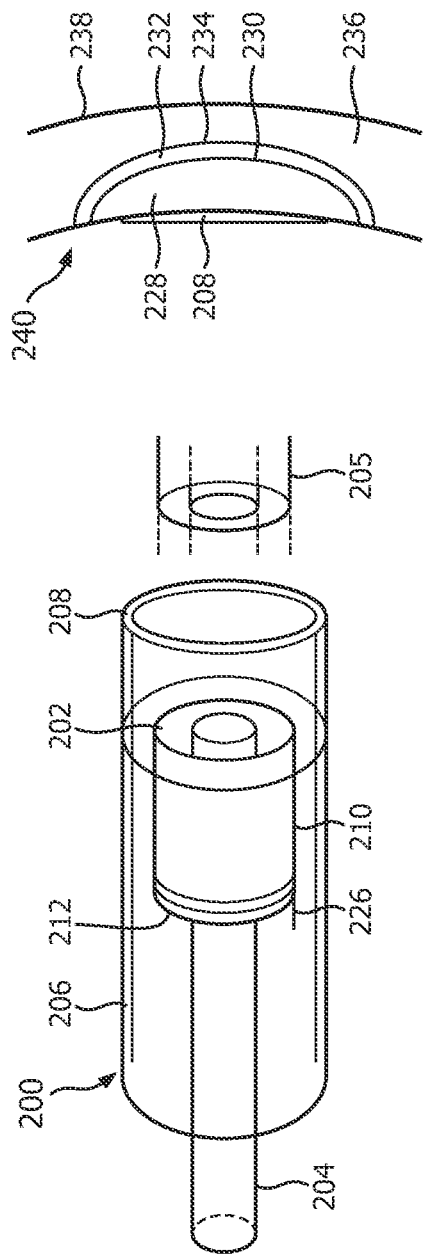
FIG. 2 provides a schematic diagram of an exemplary ablation monitoring system and a conceptual diagram, according to one possibility, of dual wavelength PA ablation monitoring.
Figure 2:
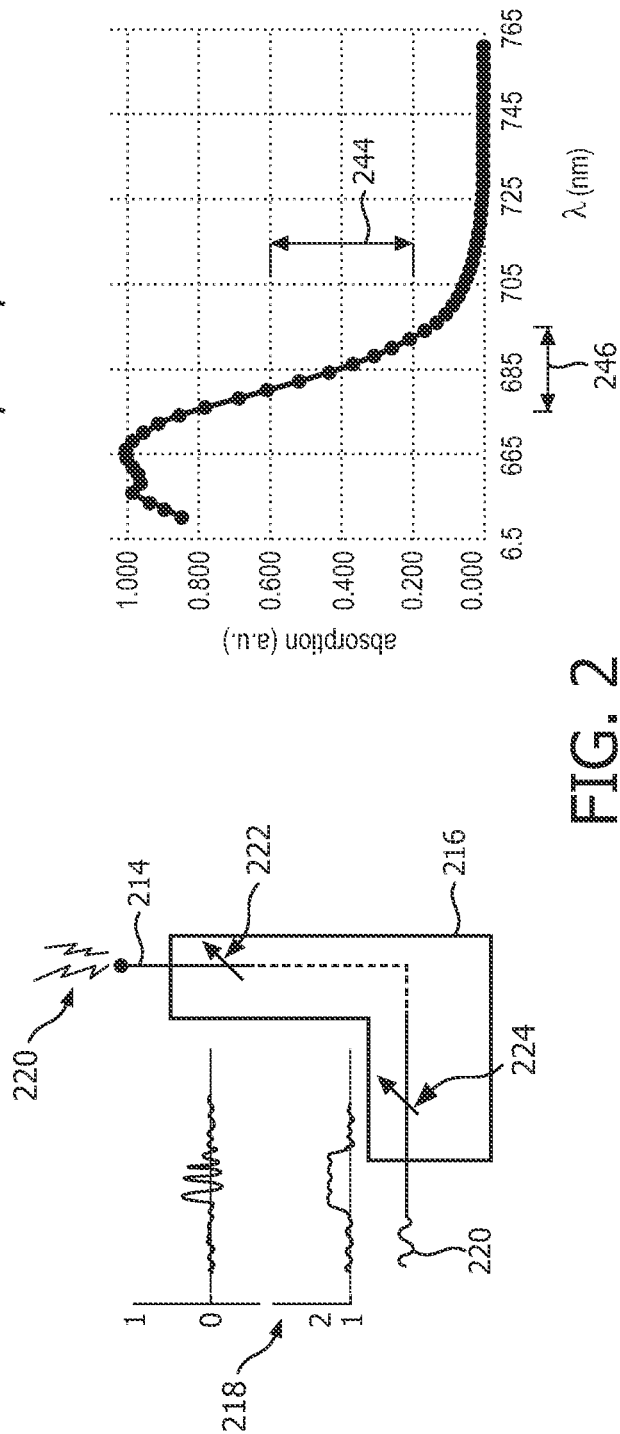

FIG. 1A depicts, approximately and for illustration purposes, two time waveforms, specifically RF waveforms, corresponding to photoacoustic absorption by biological tissue irradiated at two respective frequencies. The first waveform 102, generated by a first frequency of irradiation, or equivalently "wavelength", is shown as a solid line or curve. The second waveform 104 for a second wavelength is shown as a dotted curve. A vertical scale 106 represents the amplitude of an acoustic wave. A horizontal scale 108 indicates time. With a single flash of a light source, a laser or near-infrared light-emitting diode (LED) for example, the light, as it propagates through biological tissue will in part be absorbed, may in part be reflected and may in part pass through. The absorbed energy causes heating, expansion, and, in response, an acoustic wave which can be detected and measured. Tissue with higher light absorption has an acoustic response of greater absolute magnitude. Tissue with lower light absorption has an acoustic response of lesser absolute magnitude. Additionally, softer tissue has an acoustic response of greater and stiffer tissue of lesser absolute magnitude. The time taken by the generated acoustic wave to arrive back at an acoustic transducer, i.e., time of flight, is what is shown on the horizontal scale 108. Due to the linear relationship between time of flight and distance, the horizontal scale 108 also represents distance from the transducer to that part of the tissue whose response is at the indicated magnitude or amplitude. The distance could be, for instance, between 5 and 20 mm. As explained further below, the magnitude shown in the figure has been subject to equalization. The equalization involves depth-independent scaling. It also involves equalizing the effects of laser pulse energy variation with wavelength. The equalizing may further take into account, dynamically, wavelength-dependent attenuation in the hemorrhage zone.

The difference signal 110 in FIG. 1B approximates and represents the difference between the first and second waveforms 102, 104. The line 112 above the graph 110 having the two outwardly pointing arrowheads spatially corresponds to a hemorrhage zone in cardiac tissue. The line 114 to the left of the hemorrhage zone line 112 corresponds to the necrosed cardiac tissue. The line 116 to the right of the hemorrhage zone line 112 corresponds to healthy cardiac tissue. The hemorrhage zone is distinguished from the adjacent tissue based on the relatively enhanced magnitude visible in the graph 110. In effect, the graph portion of the adjacent tissue is largely canceled or suppressed. To produce this desired effect, the two laser wavelengths are pre-selected in accordance with a wavelength/absorption characteristic. One wavelength could be 650 nm, for example, with the other being 730 nm. From the graph 110, it is seen that the border between the necrosed tissue and the hemorrhage zone is at a tissue depth corresponding to the meeting of the arrowheads of the respective lines 112, 114. Likewise, the border between the hemorrhage zone and the healthy tissue corresponds to the meeting of the deeper-placed arrowheads of the associated lines 112, 116.

As mentioned above, the above-described technique for locating the borders is based on the idea that absorption of energy of the two wavelengths is similar both in the necrosed and healthy tissue but significantly dissimilar in the hemorrhage zone. Selection of the two wavelengths is based on the hemorrhage zone containing mostly deoxygenated hemoglobin and the healthy heart tissue containing mostly oxygenated hemoglobin. Near-infrared absorption for deoxygenated hemoglobin varies considerably over some wavelength ranges for which the absorption by oxygenated hemoglobin, and for necrotic cardiac tissue, is relatively flat.

A complicating factor in the case of the healthy tissue border is that greater absorption occurs in the depth-wisepreceding hemorrhage zone for one of the two wavelengths than for the other. Accordingly, less light penetrates through to the healthy tissue for one wavelength than for the other. For the wavelength of the light which is more attenuated, the observed absorption is less than for the less attenuated wavelength.

This results in an inter-wavelength difference that, as the hemorrhage zone gets thicker, could increasingly obscure the healthy tissue border location.

One solution is to add the criterion, in selecting the pair of wavelengths, that at least one or the other exhibit very different absorption in the hemorrhage zone as compared to in the healthy tissue. The graph for that particular wavelength is displayed in alignment underneath, for example, the difference graph 110, as a visual aid.

An alternative solution is for the apparatus to automatically measure the rate of thickening of the hemorrhage zone initially, when the obscuring effect is minimal. This rate is assumed to hold constant while ablation continues uninterrupted with the same parameter settings. Based on the observed rate, the thickness is dynamically extrapolated subsequently during the ablation. An on-screen, continually updated, marker is accordingly placed near the difference graph 110 as a fine tuning of the border location, provided ablation continues uninterrupted with the same parameter settings.

The healthy tissue border location can be compared, visually, or by the processor logic, to the location or depth at which ablation is to be halted, e.g., to prevent transmural breakthrough. The halting depth is determined by ultrasound structural imaging, for example. However, the key interest is in estimating the depth of progressing necrotic lesion, and thus the location of the hemorrhage ring is more important than the hemorrhage ring itself The line 112 can alternatively signify the location of administered PA contrast agent, with the adjacent lines 114, 116, representing background, native tissue as discussed further below.

FIGS. 1C and 1D offer, by way of illustrative and non-limitative example, alternative methods for piece-wise signal cancellation/enhancement.

As seen from FIG. 1C, an envelope waveform 120 representative of peak amplitude of the first waveform 102 can be used. Peak amplitude is not a restriction, and the envelope can follow, for example, mean absolute magnitude instead. The corresponding envelope waveform (not shown) for the second waveform 104 can be obtained, and the same difference method shown in FIG. 1B may be performed.

Nor is the combining operation causing the piece-wise cancellation/enhancement limited to subtraction of waveforms. The envelope waveforms for the two wavelengths may instead be, for example, divided to yield a quotient signal 122 as seen in FIG. 1D. Signals to be combined can also be compressed, e.g., logarithmically, in scale. The combining can, alternatively, combine lines of a reconstructed image.

The alternation between applied wavelengths in acquiring the PA data can be repeated continually for real-time monitoring of the ablation.

It is noted that each iteration of acquisition may entail stimulation with more than two wavelengths in series. From the series, a pair can be selected for combination and display, or a number of pairs can be separately combined and displayed, simultaneously, in alignment.

Also, the type of electromagnetic radiation is not limited to laser light, LED light or to light in general. For example, a microwave source with at least two distinct wavelength bands can be used instead of the light source.

FIG. 2 depicts an exemplary photoacoustic catheter 200 for two- or three-dimensional imaging of the ablated region. An annular-shaped capacitive micromachined ultrasonic transducer (CMUT) array 202 is concentrically aligned with a fiber optic cable 204. Light emitted from the fiber optic cable 204 causes an acoustic flow response from the tissue being illuminated. A portion 205 of the acoustic flow response for incidence upon the transducer array 202 is represented, conceptually, in FIG. 2 as a thick-walled, hollow cylinder concentrically aligned with the fiber optic cable 204. The cylinder can be regarded as extending to meet the transducer array 202. The array 202 is concentrically surrounded by a housing 206, of polymer for example, which may be a few millimeters in diameter. Lead wires (not shown) can run longitudinally through the housing 206 to an RF ablation ring 208 at the end of the housing. A circular sealing sheet (not shown) inside the ring 208 can be made of a substance that transmits light and ultrasound, like polymethylpentene (PMP) One example of PMP is known by the brand name TPX™. The other end of the CMUT array 202 is connected to an annular-shaped semiconductor chip 210, such as that described in U.S. Pat. No. 6,515,346 to Kemeny, or in U.S. Patent Publication 2005/0156282 to Palti, the entire respective disclosures of which are incorporated by reference herein. The chip 210 which can include any form of RAM, ROM, ASIC, PLD, or combination thereof is connected to an annular-shaped antenna 212, such as the one in Kemeny, for wireless communication with an antenna 214 of a host control unit 216. The host control unit 216 may be driven by circuitry implemented as, for example, analog electronic components, a hybrid circuit, or a solid state device comprising an integrated circuit which includes any form of RAM, ROM, ASIC, PLD, or combination thereof. The circuitry can be implemented in software, firmware or hardware or any combination thereof. An example of a wireless configuration for an interventional medical ultrasound (US) probe and its remotely-located host imaging system is described in commonly-assigned International Publication No. WO2010020939 to Peszynski et al. which is incorporated herein by reference in its entirety. The control unit 216 is connected by wire or wirelessly to a display 218 and may be configured for showing, on the display, the difference and/or quotient waveforms 110, 122 and any of the other constituent waveforms 102, 104, 120 or supplementary waveforms described hereinabove. A signal 220 embodying the above-described inventive functionality of the catheter 200, and for conveying it to the catheter, is formable by appropriately varying 222, 224 an electrical current. The signal 220 can arrive to the catheter 200 by an input wire 226, or be transmitted wirelessly by the host control unit antenna 214.

Thermal transfer from the RF ablation ring 208 forms necrosed cardiac tissue 228, as shown in FIG. 2. An outer border 230 exists between the necrosed tissue 228 and a hemorrhage zone 232. An inner border 234 exists between the hemorrhage zone 232 and healthy tissue 236. Ablation can reliably be halted before the inner border 234 reaches a distal wall 238 of the biological, and in this case, cardiac tissue 240.

Uses for the inventive method and apparatus are not limited to RF ablation or to ablation. More broadly, imaging of biological tissue for localization can be employed, for example, to locate administered PA contrast agent. In a sentinel lymph node biopsy procedure a breast cancer patient is typically injected with methylene blue dye. The dye redistribution, over the period of about 45 minutes after injection, can be monitored with photoacoustics. However, in case of some preexisting hemorrhages inside the breast tissue it may be difficult to distinguish the blue dye collection from the hemorrhage. The characteristic curve for dye, as seen in FIG. 2, specifies a decrease 244 in the absorption factor from 0.6 to 0.2 as the wavelength is increased 246 from 680 nm to 692 nm; whereas, the background, native tissue would not exhibit such a marked change in absorption with the same wavelength increase. Using two distinct wavelengths and doing the proper signal subtraction, as described in accordance with what is proposed herein, the hemorrhage signals can be suppressed. The resulting image would more clearly outline the blue dye collection areas, lymph nodes for example. This involves irradiating, in series, using either different frequencies, or different frequency bands, of electromagnetic radiation for which difference in, or ratio of, the response distinguishes over that for bordering, native tissue. Hardware implementation can use any known and suitable PA configuration, and is not limited to a catheter design.

Figure 3:
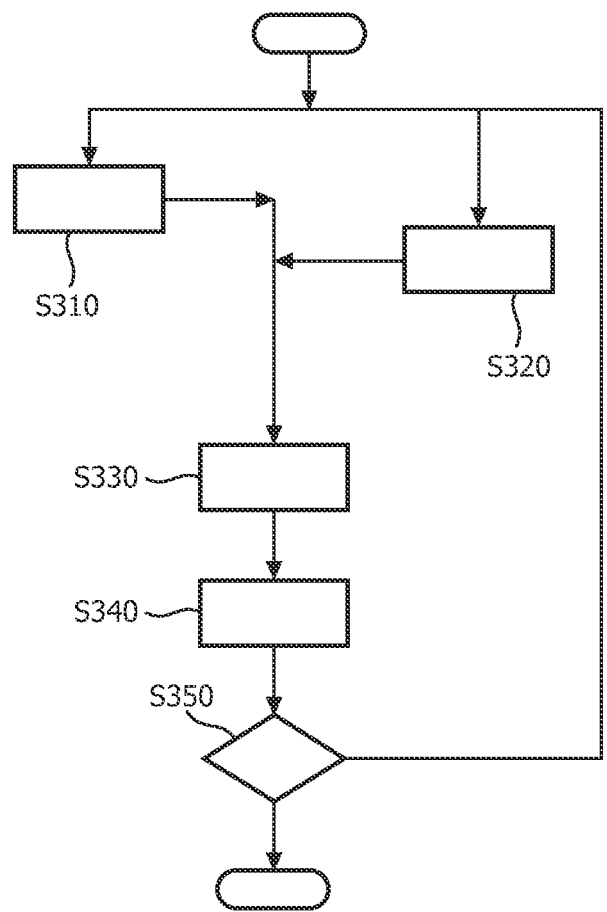
FIG. 3 is a flow chart that serves as one example of a real-time functional-imaging-based ablation, or PA contrast agent flow, monitoring method.

FIG. 3 demonstrates one possible method of monitoring through the use of imaging as described herein above. Photoacoustic or thermoacoustic data acquired through irradiation at a first wavelength, or wavelength band, is subject to depth-independent and irradiation energy equalization (step S310). The same procedure is performed for a second wavelength (step S320). The equalized data for one wavelength is combined with the equalized data of the other wavelength so as to enhance data magnitude in the hemorrhage zone relative to that for adjacent tissue (step S330). The difference signal and/or quotient signal is displayed (step S340). If the ablation or PA contrast agent locating process is to continue (step S350), return is made to the first-wavelength acquisition step S310. With real-time imaging, the steps S310-S350 are repeated continually. Many of the variations and alternatives in the above steps are set forth herein above.

Figure 4A:
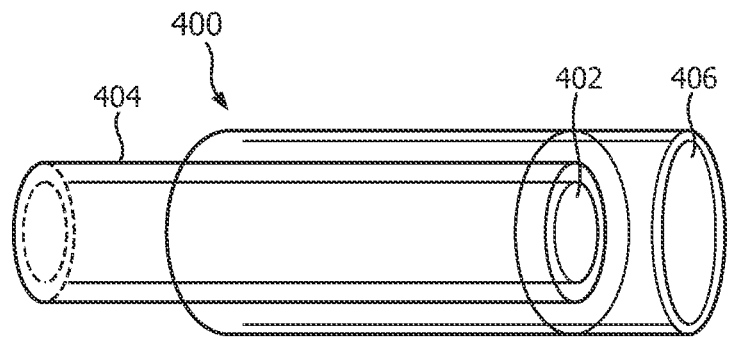
FIGS. 4A-4C provide schematic diagrams of some of the catheters suitable for cardiac RF, functional-imaging-based ablation monitoring.
Figure 4B:
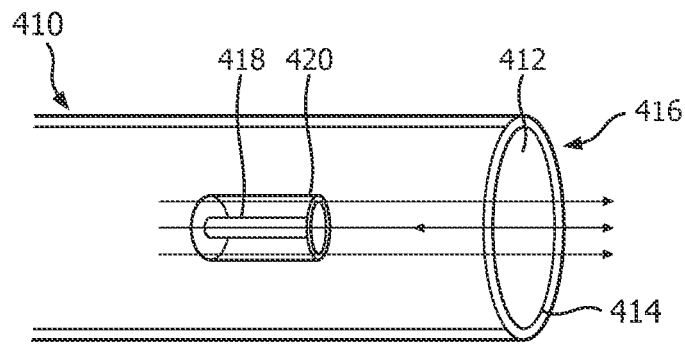
Figure 4C:
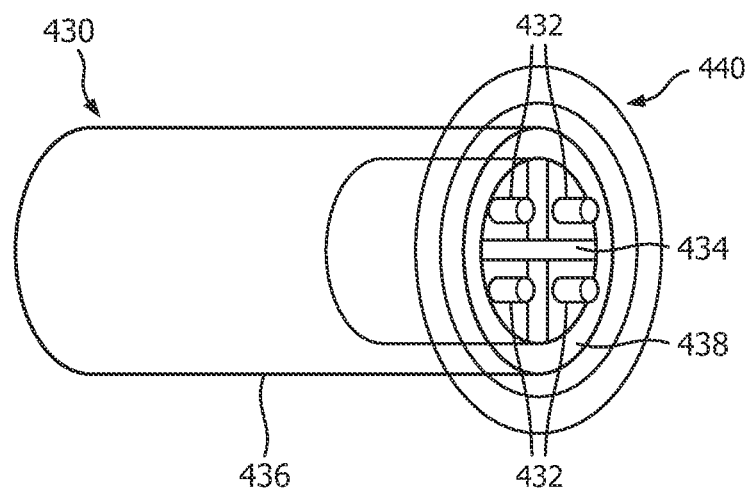

Other, alternative designs for the catheter 200 are presented in FIGS. 4A-4C. The catheter 400 in FIG. 4A differs from the catheter 200 in that a CMUT array 402 forms a central disc within a fiber optic ring 404. Accordingly, an integrated circuit (IC) (not shown) which is disc-shaped can connect to the proximal end of the CMUT array 402. United States Patent Publication 2010/0006536 to Kälvesten et al. mentions an example of a disc-shaped IC and is incorporated by reference herein in its entirety. The same annular-shaped antenna 212 can be attached. Here too, the catheter 400 has, at its distal end, an RF ablation ring 406.

Another catheter 410 implementable for the present novel method features an optically and acoustically transparent window 412 made of polymethylpentene (PMP), e.g., TPX™. The window 412 is coated with a thin layer 414, approximately 50-100 nm in thickness, of gold or platinum to act as an RF electrode 416. The layer 414 is thin enough so that light and ultrasound can nevertheless pass through without being attenuated significantly. The present inventors have found that a uniform ablation can be created with much lower powers than needed with traditional RF electrodes. An ultrasound transducer 418 is concentrically surrounded by an annular-shaped light source 420 provided for PA operation. Ultrasound generated by absorption of the light includes an acoustic-response-flow portion incident upon the transducer 418, that portion being concentrically aligned with the light source 420. The catheter 400 may be provided with an ultrasound-only imaging mode, in which the transducer 418 both emits ultrasound and receives ultrasound reflected back in response, as indicated in FIG. 4B by the oppositely directed arrowheads.

FIG. 4C shows a PA/US catheter 430 for illuminating a larger area of the tissue 240. Four optical fibers 432 are provided. A cross-shaped CMUT array 434 can receive the ultrasound coming back from the larger illuminated area. The distal end of a catheter housing 436 has an RF ablation ring 438. RF propagation to the anode is represented symbolically in FIG. 4C by the rings 440 concentrically extending from the RF ablation ring 438.

As a further example of a catheter, a fluid focus (FF) lens may be substituted for the CMUT array shown in FIG. 4A. One possible implementation is a modification of the embodiment disclosed in commonly-assigned International Publication No. WO 2010/146532 to Shahzad et al. (hereinafter "the '532 application"). The modification would secure the lens within the annular fiber-optic waveguide 404 extending within the catheter housing. By virtue of the FF lens, the catheter may also be used in ultrasound-only mode to acquire information on tissue elastic properties. This information may be utilized to independently image the ablation site in real time, an example of which is provided in the '532 application. The PA and US modes can be alternated continually to provide the PA- and tissue-elastic-imaging in real time.

In another variation, four fiber optic waveguides optically coupled to the four corners of the FF lens can substitute for the single waveguide 404 in the above-described FF embodiment.

In yet another version, the FF lens can be disposed side-looking. For example, the catheter in commonly-assigned U.S. Patent Publication 2010/280504 to Manzke et al., the entire disclosure of which is incorporated herein by reference, can be implemented with a reflector to reflect an ultrasound path 90 degrees into an ultrasound transducer longitudinally disposed within the catheter. The side opening is concentrically surrounded on the surface of the catheter housing first by an LED ring and then by an RF cathode. A good reflector, e.g., of metal or air, can be used to minimize the assembly. The closeness of the LEDs in the ring to the tissue being illuminated leads to a compact design.

In all of the above-discussed catheter embodiments, the ultrasound transducer may be excluded, and provided elsewhere, as in an external probe.

It is also within the intended scope of the invention that the ablation ring may be excluded. Ablation can be instead be effected by emitting a beam from the catheter. Optionally, ablation could be performed by a high intensity focused ultrasound (HIFU) device or other device external to the catheter.

Functional imaging for localization in biological tissue entails measuring a response in the tissue to electromagnetic radiation. A catheter for real-time monitoring of cardiac ablation is employed to distinguish a hemorrhage zone from the sandwiching necrotic and healthy tissue, or to distinguish exogenous photoacoustic contrast agent from bordering native tissue. A pair of wavelengths is selected for differential absorption of the radiation in, correspondingly, the hemorrhage zone or where the contrast agent exists, and relatively similar absorption elsewhere. Near-infrared laser or LED light may be used photoacoustically to serially acquire the two datasets to be compared, each representative of a time waveform. Alternatively, acquisition is for a pair of wavelength bands of microwave-induced thermoacoustic data. In either case, the members of the dataset pair are combined by subtraction or division to effect the piece-wise cancellation/enhancement for display of the resulting signal in real time.

Although methodology according to what is proposed herein can advantageously be applied in providing medical diagnosis for a human or animal subject, the intended scope of claim coverage is not so limited. More broadly, enhanced photoacoustic imaging, in vivo, in vitro or ex vivo is envisioned.

The proposed technology addresses the need to monitor with good precision the catheter-based RF ablation lesion formation for treating atrial fibrillation (AF), supraventricular tachycardia (SVT), and other types of ventricular arrhythmia in the electrophysiology (EP) lab.

While the invention has been illustrated and described in detail in the drawings and foregoing description, such illustration and description are to be considered illustrative or exemplary and not restrictive; the invention is not limited to the disclosed embodiments.

For example, instead of a single pulse of electromagnetic energy, the intensity may be modulated by firing multiple shots to create a train of pulses.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache and RAM.

A single processor or other unit may fulfill the functions of several items recited in the claims. The mere fact that certain measures are recited in mutually different dependent claims does not indicate that a combination of these measures cannot be used to advantage.

What is claimed is:

1. An apparatus configured for using functional imaging for localization of biological tissue, said apparatus comprising:
   an electromagnetic-radiation emitter configured for emitting electromagnetic radiation to said biological tissue;
   an ultrasound transducer configured for receiving ultrasound from said biological tissue responsive to said emitting; and
   a photoacoustic imaging device configured for: operating said electromagnetic-radiation emitter; operating said ultrasound transducer; from the received ultrasound, measuring responses in the biological tissue to electromagnetic radiation; and, based on said responses, distinguishing, within the biological tissue, one or both of (i) a hemorrhage zone, disposed between (i)(a) healthy tissue and (i)(b) ablated tissue, from said healthy and ablated tissue by identifying a border between said hemorrhage zone and said healthy tissue and by identifying a border between said hemorrhage zone and said ablated tissue, and (ii) a contrast agent from bordering native tissue,
   wherein said distinguishing entails combining, via said photoacoustic imaging device, datasets acquired, via said transducer, by electromagnetic irradiation, via said emitter, at different frequencies or frequency bands,
   wherein the datasets serve as measures of absorption by said biological tissue of the electromagnetic radiation, and
   wherein the different frequencies or frequency bands are (iii) selected for (iii)(a) differential absorption of radiation in, correspondingly, the hemorrhage zone or where the contrast agent exists and (iii)(b) relatively similar absorption elsewhere in the healthy tissue, the ablated tissue, and the bordering native tissue.

2. The apparatus of claim 1, wherein said combining of said datasets enhances a data magnitude in said hemorrhage zone relative to that, respectively, for adjacent healthy and ablated tissue.

3. The apparatus of claim 1, further comprising a display for displaying a signal representative of the combined datasets, wherein said displaying reflects said distinguishing.

4. The apparatus of claim 3, wherein the apparatus comprises one or more integrated circuits communicatively connected to at least one of said ultrasound transducer for the acquiring of said datasets and said electromagnetic-radiation emitter for said irradiating.

5. The apparatus of claim 1, wherein said combining forms a combined dataset; and wherein, in the acquiring, data of one of the datasets to be combined in forming said combined dataset is acquired before acquisition, via said transducer, commences for data of another dataset being combined in said forming of said combined dataset.

6. The apparatus of claim 1, wherein said combining combines a pair of said datasets, and wherein one of said datasets of said pair is a dataset of a frequency or a frequency band, and wherein the other of said datasets of said pair is respectively of a frequency or of a frequency band, such that said datasets of said pair are both of respective frequencies that differ or both of respective frequency bands that differ.

7. The apparatus of claim 6, further wherein said combining of said pair of said datasets comprises at least one of subtraction and division.

8. The apparatus of claim 6, further wherein each of said datasets of said pair is representable as a time waveform.

9. The apparatus of claim 7, wherein said photoacoustic imaging device is configured for at least one of the subtracting to yield a difference signal and the dividing to yield a quotient signal, the apparatus further comprising
   a display, wherein said photoacoustic imaging device is configured for, via said display, displaying at least one of said difference and quotient signal, respectively.

10. The apparatus of claim 6, further wherein said combining of said pair of datasets is performed by subtraction.

11. The apparatus of claim 1, wherein said localization includes monitoring, at least via said measuring and said distinguishing, of the biological tissue performed in real time.

12. The apparatus of claim 11, further wherein said monitoring entails monitoring of cardiac ablation.

13. The apparatus of claim 1, further wherein said photoacoustic imaging device is further configured for performing a depth-independent equalization that takes into account wavelength-dependent attenuation in said hemorrhage zone.

14. The apparatus of claim 1, further comprising a catheter that houses said ultrasound transducer.

15. The apparatus of claim 1, wherein said ablated tissue immediately adjoins said hemorrhage zone to form said border that exists between said hemorrhage zone and said ablated tissue and that defines an outer extent of both said ablated tissue and said hemorrhage zone, and wherein said healthy tissue immediately adjoins said hemorrhage zone to form said border that exists between said hemorrhage zone and said healthy tissue and that defines an outer extent of both said healthy tissue and said hemorrhage zone.

16. The apparatus of claim 1, wherein said contrast agent comprises methylene blue dye.

17. The apparatus of claim 11, further comprising a display, and an ablation device for ablating said biological tissue, said apparatus being configured for said distinguishing of said hemorrhage zone and for performing, via said ablation device, ablation to result in said ablated tissue, wherein said photoacoustic imaging device is further configured for, during said ablation, displaying, via said display, updated in real time to reflect said monitoring, a real-time spatial representation of, collectively, said hemorrhage zone adjoined both by said healthy tissue and said ablated tissue.

18. The apparatus of claim 11, further comprising an ablation device, said apparatus being configured for structural imaging and for said distinguishing of said hemorrhage zone, said apparatus being further configured for performing, via said ablation device, ablation to result in said ablated tissue, wherein said apparatus is further configured for, automatically, without need for user intervention, halting said ablation in real-time response to said border between said hemorrhage zone and said healthy tissue reaching, during said monitoring, in accordance with said structural imaging, a depth at which ablation is to be halted.

19. The apparatus of claim 1, wherein said biological tissue comprises cardiac tissue, and wherein said responses are measured, by said measuring, in cardiac tissue.

20. A method for using functional imaging for localization of biological tissue, said method comprising:
emitting, via an electromagnetic-radiation emitter, electromagnetic radiation to interrogate biological tissue;
via an ultrasound transducer, receiving, from said biological tissue, responses to the emitted electromagnetic radiation which are elicited by the interrogation;
measuring, via a processor, said responses; and,
via said processor, based on said responses, distinguishing, within the biological tissue, one or both of (i) a hemorrhage zone, disposed between (i)(a) healthy tissue and (i)(b) ablated tissue, from said healthy and ablated tissue by identifying a border between said hemorrhage zone and said healthy tissue and by identifying a border between said hemorrhage zone and said ablated tissue. and (ii) a photoacoustic contrast agent from bordering native tissue, based upon the responses,
wherein said distinguishing entails combining, via the processor, datasets acquired, via said transducer, by said electromagnetic irradiation, via said emitter, at different frequencies or frequency bands,
wherein the datasets serve as measures of absorption by said biological tissue of the electromagnetic radiation, and
wherein the different frequencies or frequency bands are (iii) selected for (iii)(a) differential absorption of radiation in, correspondingly, the hemorrhage zone or where the contrast agent exists and (iii)(b) relatively similar absorption elsewhere in the healthy tissue, the ablated tissue, and the bordering native tissue.

21. A non-transitory computer software product for using functional imaging for localization of biological tissue comprising a computer-readable medium embodying a computer program that includes instructions executable by a processor for performing a plurality of acts, from among said plurality there being the acts of:
measuring responses in the biological tissue to electromagnetic radiation; and
based on the responses, distinguishing, within the biological tissue, one or both of (i) a hemorrhage zone, disposed between (i)(a) healthy tissue and (i)(b) ablated tissue, from said healthy and ablated tissue by identifying a border between said hemorrhage zone and said healthy tissue and by identifying a border between said hemorrhage zone and said ablated tissue, and (ii) a photoacoustic contrast agent from bordering native tissue,
wherein said distinguishing entails combining datasets acquired, via an ultrasound transducer, by electromagnetic irradiation, via an electromagnetic-radiation emitter, at different frequencies or frequency bands,
wherein the datasets serve as measures of absorption by said biological tissue of the electromagnetic radiation,
wherein the different frequencies or frequency bands are (iii) selected for (iii)(a) differential absorption of radiation in, correspondingly, the hemorrhage zone or where the contrast agent exists and (iii)(b) relatively similar absorption elsewhere in the healthy tissue, the ablated tissue, and the bordering native tissue, and;
wherein, from among said plurality, there are, in addition, the acts of:
emitting, via said emitter, said electromagnetic radiation to interrogate said biological tissue;
via said transducer, receiving, from said biological tissue, said responses to the emitted electromagnetic radiation which are elicited by the interrogation and which are to be measured in said measuring; and at least one of:
causing display of a signal representative of the combined datasets, wherein the displaying reflects said distinguishing; and,
based on a border between said hemorrhage zone and said healthy tissue advancing sufficiently to spatially meet a threshold, halting ablation that forms said ablated tissue.

22. The non-transitory computer software product of claim 21, wherein said biological tissue comprises cardiac tissue, and wherein said responses are measured, by said measuring, in cardiac tissue.

* * * * *